United States Patent [19]

Kirwan, Sr. et al.

[11] Patent Number: 4,890,610

[45] Date of Patent: Jan. 2, 1990

[54] BIPOLAR FORCEPS

[76] Inventors: Lawrence T. Kirwan, Sr., 81 Island Creek Rd., Duxbury, Mass. 02332; Lawrence T. Kirwan, Jr., 203 Indian Pond Rd., Kingston, Mass. 02364

[21] Appl. No.: 361,837

[22] Filed: Jun. 5, 1989

Related U.S. Application Data

[63] Continuation-in-part of Ser. No. 232,559, May 15, 1988, abandoned, which is a continuation of Ser. No. 83,375, Aug. 15, 1987, abandoned.

[51] Int. Cl.⁴ ............................................ A61B 17/36
[52] U.S. Cl. ....................................................... 606/51
[58] Field of Search ...................... 128/303.13, 303.19, 128/321; 200/61.58 R, 157; 219/234

[56] References Cited

U.S. PATENT DOCUMENTS

| | | | |
|---|---|---|---|
| 3,643,663 | 2/1972 | Suttar | 128/303.17 |
| 4,041,952 | 8/1977 | Morrison, Jr. | 128/303.17 |
| 4,054,143 | 10/1977 | Bauer | 128/303.17 |
| 4,128,099 | 12/1978 | Bauer | 128/303.17 |
| 4,137,919 | 2/1979 | Farin et al. | 128/303.17 |
| 4,353,371 | 10/1982 | Cosman | 128/303.17 |
| 4,492,231 | 1/1985 | Auth | 128/303.17 |
| 4,567,890 | 2/1986 | Ohta et al. | 128/303.13 |

*Primary Examiner*—Raymond A. Nelli

[57] ABSTRACT

This application discloses a pair of bipolar forceps for use in medicine the forceps having one piece blade portions, the center of which is coated with a plastic material and which has an integral connector formed at one end of the overcoated plastic and a terminal end of each of the blade portions.

11 Claims, 1 Drawing Sheet

BIPOLAR FORCEPS

This is a continuation-in-part of co-pending application Ser. No. 232,559 filed on Aug. 15, 1988, now abandoned, which is a continuation of 083,375 filed on Aug. 10, 1987, now abandoned.

BACKGROUND OF THE INVENTION

Field of the Invention

This invention relates to surgical forceps and more specifically to bipolar forceps.

BRIEF DESCRIPTION OF THE DRAWINGS

Further details are explained below with the help of the example(s) illustrated in the attached drawings in which.

SUMMARY OF THE INVENTION

Figure 1:
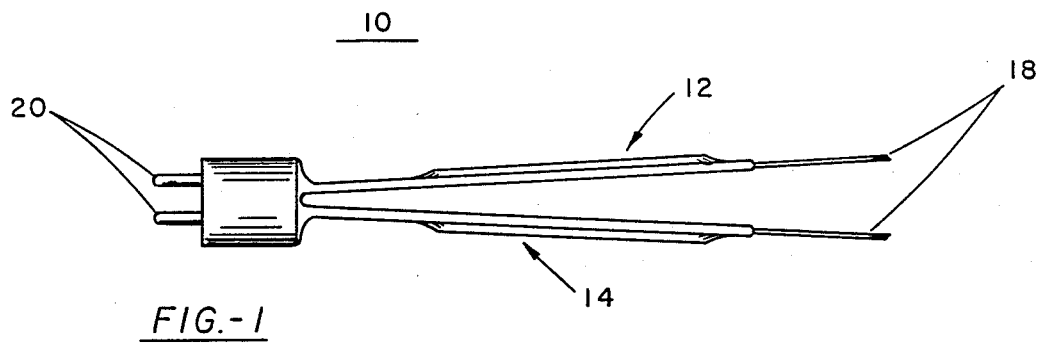
FIG. 1 is a side elevational view of the bipolar forceps according to the present invention.
Figure 2:
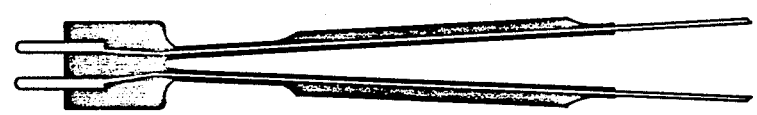
FIG. 2 is a cross section taken through the bipolar forceps taken on line 2—2 of FIG. 1.
Figure 3:
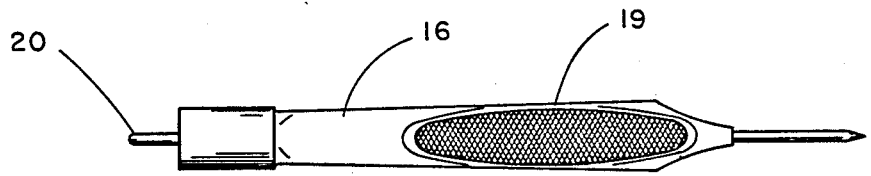
FIG. 3 is a top plan view of the bipolar forceps shown in FIG. 1.
Figure 4:
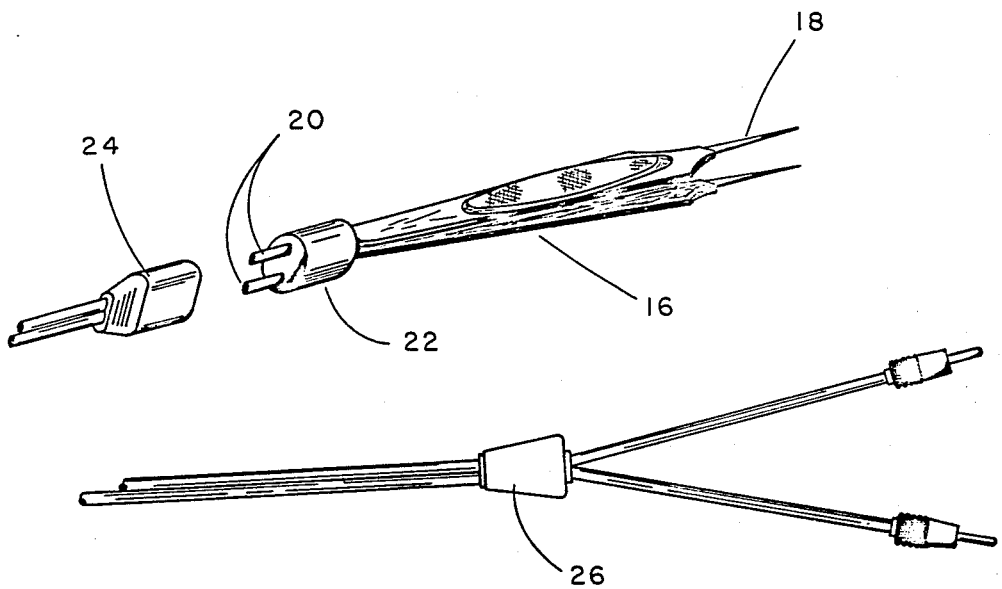
FIG. 4 is a perspective view of the bipolar forceps shown in FIG. 1.

The invention disclosed herein comprises a set of bipolar forceps manufactured by coining unitary first and second blade portions which are then placed in a mold and overmolded with a plastic of choice. The plastic leaves a portion of one terminal end of the blade portion exposed to form a tip. Each of the blade portions has its terminal end remote from the tip 18 formed into a connector pin. At the overmolding step the area adjacent the connector pins may be formed into a connector portion.

DESCRIPTION OF THE PREFERRED EMBODIMENT(S)

There is shown in the drawings an pair of bipolar forceps 10 comprising a first tine or blade portion 12 and a second blade portion 14.

The bipolar forceps 10 are manufactured by coining the unitary first and unitary second blade portions 12, 14. Each of them is placed in a mold and overmolded with a plastic of our choice, for example, polystyrene, PDC #11-10 Green PS manufactured by the Down Chemical Co. or PVC product #GA-90990-745-Green manufactured by Global Products Corp., forming a coat 16. The plastic leaves a portion of one terminal end of the blade portion exposed to form a tip 18. The plastic should be stable under gamma radiation. If the bipolar forceps 10 is intended to be disposable, then an inexpensive plastic which fits the other requirements should be utilized. Obviously the plastic should have sufficient dielectric strength for the currents and voltages which are normally encountered in bipolar type instruments. The first and second blade portion 12, 14 function as single or in line electrical conductors. A portion of the coat 16 is scribed externally to form a body portion 19 which as shown in cross section provides an arced configuration. Electrically speaking one of the blade portions 12, 14 will carry a positive current while the other carries a negative current. Each of the blade portions 12, 14 has its terminal end remote from the tip 18 formed into a connector pin 20. At the overmolding step the area adjacent the connector pins 20 is formed into a connector portion 22. This connector portion 22 is configured as an enlarged collar portion. The end result is a unitary bipolar forceps 10 which includes the first and second blade portions 12, 14, having a predetermined area with a coat 16 and a connector portion 22 with the exposed tips 18 and connector pins 20. The first and second blade portions 12, 14 are shown in angular, spaced relation to each other although they may be in spaced, parallel relation to each other if desired. The tips 18 may be straight. They may be bent upwardly first and down slightly to provide an oattation tip. The tips may be bent in other ways if desired.

The bipolar forceps 10 are used for manipulating tissue and at the surgeon's desire coagulating or desiccating the tissue by a voltage from an electrosurgical generator (not shown) connected to the bipolar forceps 10. The electrosurgical generator is connected to the connector pins 20 by an assembly which includes a socket 24 at one end and a pair of banana pin connectors at the other end connected together by a pair of wires. From the each of the banana pin connectors a single wire runs to the keeper 26 and from that point to the socket 24, the single wires are attached and run in parallel.

The bipolar forceps are usually sterilized after surgical use. Hot sterilization will cause the plastic coating to melt or deteriorate distorting the first and second tine portions requiring that the bipolar forceps be disposed of.

An acceptable method of sterilization is steam autoclaving. Typically the instruments are wrapped in muslin covers which are placed on the sterilizer unit and then placed inside the sterilizer chamber. When the sterilizer unit is turned on the bipolar forceps will be exposed to steam at 250 degrees F. and pressure for a period of twenty minutes. A variation of the mentioned procedure exposes the instruments to pressure and steam at 270 degrees F. for a period of ten minutes. Both procedures are sufficient to deteriorate the plastic. On sterilization the plastic will melt slightly, causing loss of alignment and dimensions of the first and second tine portions. The plastic itself becomes brittle because of loss of plasticizers. The bipolar forceps are no longer acceptable for use and must be disposed of.

What we claim is:

1. A microsurgical bipolar forceps comprising elongated, unitary, coined, first and second tine portions and a first and second housing portions, each of tine portions having a first and second terminal ends and the first tine portion having a first blade, and the second tine portion having a second blade, each of the first and second blades including a front terminal end and a rear terminal end and the first blade positioned within the first housing and the second blade positioned within the second housing, the first terminal end providing a tip and the second terminal end providing a connector pin, the tip extending longitudinally from the front terminal end and the connector pin extending longitudinally from the rear terminal end, the first and second tine portions being formed of a material capable of carrying an electric current, the first housing portion overmolded and covering the first blade and the second housing portion overmolded and covering the second blade and the first and second housing portions formed of a material that will distort the first and second tine portions when the forceps are exposed to steam at 250 degrees F. and pressure for a period of twenty minutes, the connector pin of each blade adapted to engage an electric socket.

2. The microsurgical bipolar forceps set forth in claim 1 wherein the blades form the electric connector means.

3. The microsugical bipolar forceps set forth in claim 1 wherein the first and second tine portions are in spaced relation to each other.

4. The microsurgical bipolar forceps set forth in claim 3 wherein the first and second tine portions are in parallel relation to each other.

5. The microsurgical bipolar forceps set forth in claim 1 wherein the housing of each of the first and second tine portions includes an externally arced body portion.

6. The microsurgical bipolar forceps set forth in claim 5 wherein the body portions have striations formed therein.

7. The microsurgical bipolar forceps set forth in claim 5 wherein the blades form the electric connector means.

8. A microsurgical bipolar forceps as recited in claim 1, wherein the first and second housing portions formed of a material that will distort the first and second tine portions when the forceps are exposed to steam at 270 degrees F. and pressure for a period of ten minutes.

9. A method of forming a pair of disposable microsurgical bipolar forceps, the bipolar forceps including elongated, unitary, first and second tine portions, each of the tine portions having first and second terminal ends and the first tine portion having a first blade and the second tine portion having a second blade, the method comprising the steps of:

coining, the first and second blade portions, placing each of the first and second blade portions in a mold and overmolding the first and second blade portions with a plastic material, the plastic material being one that will distort the first and second tine portions when the forceps are subject to heat above 250 degrees F. and pressure for a period of twenty minutes, the overmolding providing exposed first and second terminal ends, the first terminal end forming a tip, the second terminal end formed into a connector pin.

10. The method of forming a pair of microsurgical bipolar set forth in claim 9 further comprising the step of: the forming the area adjacent the connector pins into a connector portion.

11. A method of forming a pair of disposable microsurgical bipolar forceps as recited in claim 9, wherein the first and second housing portions formed of a material that will distort the first and second tine portions when the forceps are exposed to steam at 270 degrees F. and pressure for a period of ten minutes.

* * * * *